United States Patent [19]

Monnier et al.

[11] Patent Number: 4,925,986
[45] Date of Patent: May 15, 1990

[54] PREPARATION OF ALDEHYDES FROM UNSATURATED TERMINAL EPOXIDES

[75] Inventors: John R. Monnier, Fairport; Peter J. Muehlbauer, Spencerport; Howard M. Low, Rochester, all of N.Y.

[73] Assignee: Eastman Kodak Company, Rochester, N.Y.

[21] Appl. No.: 337,595

[22] Filed: Apr. 13, 1989

[51] Int. Cl.$^5$ .................... C07C 45/67; C07C 45/70
[52] U.S. Cl. .................................... 568/450
[58] Field of Search ................. 568/450, 427

[56] References Cited

U.S. PATENT DOCUMENTS

| | | | |
|---|---|---|---|
| 1,906,833 | 5/1933 | Baur | 568/450 |
| 2,503,050 | 4/1950 | Jacobs et al. | 568/450 |
| 2,628,255 | 2/1953 | Sexton et al. | 568/450 |
| 2,686,205 | 8/1954 | Gasson et al. | 568/450 |
| 2,694,090 | 11/1954 | Wild et al. | |
| 3,067,256 | 12/1962 | Fischer et al. | |
| 3,465,043 | 9/1969 | Lini et al. | |
| 4,495,371 | 1/1985 | Neri et al. | |
| 4,621,150 | 11/1986 | Hirai et al. | |
| 4,650,908 | 3/1987 | Pope | |

FOREIGN PATENT DOCUMENTS

| | | | |
|---|---|---|---|
| 465177 | 5/1950 | Canada | 568/450 |
| 521729 | 5/1956 | Canada | 568/450 |
| 331185 | 6/1930 | United Kingdom | 568/450 |
| 690383 | 4/1953 | United Kingdom | 568/450 |

*Primary Examiner*—Werren B. Lone
*Attorney, Agent, or Firm*—Robert A. Linn

[57] ABSTRACT

Crotonaldehyde is produced by contacting 3,4-epoxybutene, i.e. butadiene monoxide, with a halide-containing catalyst such as a hydrogen halide or metal halide. The process is preferably conducted in the vapor phase. Other unsaturated aldehydes can be produced from other unsaturated terminal epoxides.

13 Claims, No Drawings

PREPARATION OF ALDEHYDES FROM UNSATURATED TERMINAL EPOXIDES

FIELD OF THE INVENTION

This invention relates to a catalytic method for the preparation of unsaturated aldehydes. In the process, an unsaturated terminal epoxide is contacted with a halide catalyst. In a particular aspect, the invention pertains to the preparation of crotonaldehyde from butadiene monoxide. Preferably, the catalyst is on a support.

RELATED ART

Lini U.S. Pat. No. 3,465,043 teaches that crotonaldehyde can be made from butadiene monoxide in the presence of a rhodium-containing catalyst. The catalyst may be a compound such as bis carbonyl rhodium (II) chloride dimer, or rhodium (III) chloride trihydrate.

Alper et al *J. Org. Chem.* 41(22) 3611–3613 (1976) teaches that vinyl epoxides give $\alpha, \beta$- unsaturated aldehydes when contacted with a catalytic amount of molybdenum hexacarbonyl.

The above described prior art processes are not entirely satisfactory because of the nature of the catalysts employed. More particularly, the catalysts of the prior art are relatively expensive, or relatively unsuitable because of their thermal and/or chemical instability. Hence, a need exists for a process for making unsaturated aldehydes from unsaturated epoxides using a catalyst which exhibits thermal and chemical stability, is readily available, and comparatively inexpensive. Until the present invention, it was not known that the materials used as catalysts in the present process could be used to prepare unsaturated aldehydes from unsaturated epoxides. Hence, it is believed that the present invention presents a significant advance in the art.

SUMMARY OF THE INVENTION

This invention relates to the preparation of unsaturated aldehydes from unsaturated terminal epoxides. The process involves opening of the epoxide ring, migration of a hydrogen species from one ring carbon to another position to give a carbonyl group, and also a migration of a carbon to carbon double bond from one position in the molecule to another. The mechanism by which these multiple transformations take place is not known at this time.

Aldehydes are widely used as chemical intermediates. So are compounds with olefinic double bonds. Hence, the products of the present invention are highly useful as intermediates since they contain both reactive systems, the aldehyde group and the olefinic linkage.

DESCRIPTION OF PREFERRED EMBODIMENTS

This invention provides a process for the preparation of an unsaturated aldehyde, said process comprising isomerizing a terminal epoxide having an olefinically unsaturated carbon atom in a position which is adjacent to the epoxide ring in said epoxide, by contacting said epoxide with a catalytic quantity of a catalyst (preferably a supported catalyst) at a temperature at which said isomerization takes place, said catalyst comprising a halide selected from hydrogen halides having the formula $HX$, and metal halides having the formula $MX_n$, wherein M is a metal selected from Groups IA, IIA, IIIA, IB, IIB, IVB, VB, VIB, VIIB, and the iron subgroup metals of the Periodic Table, X is a halogen, and n is a small whole number equal to the valence of the metal M.

The terminal, unsaturated epoxides employed in the process of this invention have the formula:

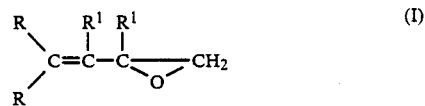

wherein the substituents indicated by R and $R^1$ are hydrogen or organic substituents which do not interfere with the process. The organic substituents preferably (i) are stable or substantially stable under the reaction conditions employed, (ii) are unreactive or substantially unreactive with the catalyst, the product, and other moieties within molecules of the starting epoxide, and (iii) do not interfere with the process by steric hindrance, or by poisoning the catalyst, or by some other undesired mechanism. For the purpose of this invention, such substituents meeting or substantially meeting the above three criteria are designated "inert substituents".

As indicated above, when all substituents illustrated by R or $R^1$ in the above structural formula are hydrogen, the compound is the material referred to herein as "butadiene monoxide." The invention is not critically dependent on the nature of the substituents bonded to the carbon atoms. A wide variety of substituents may be present, provided that they effectively meet the criteria set forth above. It is preferred that the moieties indicated by R in the above formula be selected from hydrogen and alkyl groups that have up to about 4 carbon atoms, and the substituents represented by $R^1$ be selected from hydrogen and alkyl groups having up to about two carbon atoms. Other alkyl groups can also be used, if desired. As already indicated, a highly preferred reactant is butadiene monoxide.

The products of this invention are unsaturated aldehydes:

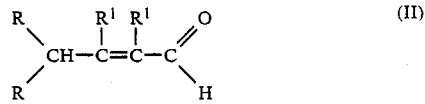

wherein R and $R^1$ have the same significance as above.

The catalyst employed in the process of this invention can be selected from a wide variety of metal halides, particularly binary metal halides. Thus, the catalyst may be a halide of an alkali metal, such as lithium or cesium. The catalyst may also be a halide of an alkaline earth metal such as barium. Likewise, the catalyst may be selected from a Group IIB metal such as zinc or cadmium. For the metals mentioned above, it is preferred that the halogen be the iodide ion, since iodides of these metals have the desired reactivity. It is to be understood however, that this invention is not limited to the use of iodides as catalysts. For example, iodides, chlorides and bromides of metals in the other groups and subgroup of the Periodic Table mentioned above, can be employed in the process of this invention. For example, the chlorides and bromides of zinc, copper, aluminum, titanium, vanadium, chromium, manganese and iron can be employed as catalysts in this process.

The catalyst employed may also be a hydrogen halide such as hydrogen chloride, hydrogen bromide, and hydrogen iodide. Preferably, the catalysts are substantially free of water. In other words, it is preferred that the hydrogen halide catalysts be substantially anhydrous, and that the metal halide catalysts not be hydrated.

Of the catalysts, certain are preferred. With regard to the hydrogen halides, hydrogen iodide is the preferred catalyst. It is also preferred that the hydrogen halides be used with a metal oxide support such as those mentioned below. With regard to the halides of Groups IA and IIA of The Periodic Table, the iodides are preferred. Stated another way, it is preferred to use the iodides of the alkali metals and the alkaline earth metals. For the Group IIIA metal halides, aluminum halides, e.g. $AlCl_3$ and $AlBr_3$, are preferred.

With regard to the transition metal (Groups IIIB, IVB, VB, VIB, VIIB, and the iron-subgroup) and Groups IB and IIB halides, the halide salts of the first member of each group is preferred. Thus for this invention, it is preferred to use the halides of titanium, vanadium, chromium, manganese, iron, copper and zinc. The chlorides and bromides of these metals are preferred.

The results obtained in this invention suggest that halides of Group IIIB can be used as catalysts in this invention. However, such materials are comparatively expensive or unavailable; hence, other catalysts such as those described and exemplified herein are more preferred.

The catalyst employed is heterogeneous, i.e., not soluble in the reaction mixture. The catalyst can be used with either gaseous or liquid reaction systems. When desired, the reaction mixture can contain an inert liquid reaction medium to facilitate contacting the reactants, e.g., when the olefin oxide is a solid at reaction temperature. The liquid reaction medium may be selected from liquid hydrocarbons or ethers, such as hexanes or tetrahydrofuran. As discussed below, when a gaseous or vapor phase reaction is used, the epoxide may be admixed with a diluent.

It is presently preferred to apply the catalyst to a solid support for efficient use of the catalyst. Typical catalyst supports include calcium oxide, magnesium oxide, zinc oxide, alumina, e.g., $\gamma$-alumina or activated aluminas, silica-alumina, silica, and the like, as well as mixtures of the above. Other inert supports typically used as catalyst supports can be used.

When a catalyst support is employed, the loading level of metal or hydrogen halide on the support typically falls within the range of about 0.5 up to 50 weight percent, calculated as the halide and based on the total weight of finished catalyst. Preferably, the loading level of the catalyst falls within the range of from about 1 to about 30 weight percent metal halide or hydrogen halide, with loading levels in the range of from about 1 to about 20 weight percent being most preferred.

The actual physical form of the catalyst support is not particularly important. While the form of the catalyst support has little effect on catalyst activity, practical considerations such as ease of heat transfer, mass transfer, pressure drop due to fluid flow restrictions, efficiency of gas-liquid-solid contacting, catalyst durability, and the like make the use of defined shapes such as spheres, pellets, extrudates, rings, saddles, and the like, preferred catalytic materials.

Those of skill in the art will also recognize that the catalysts employed in the practice of the present invention can include additional components which may modify catalyst activity and/or selectivity. Thus, additives may be incorporated into the finished catalyst to aid catalyst preparation, e.g., binders, die lubricants, and the like; or to reduce the cost of catalyst preparation; or to extend the operating ranges for reaction temperature and/or pressure; or to increase catalyst lifetime under reaction conditions. It is recognized, of course, that some additives are suitably employed in very low levels (i.e., milligrams of additive per gram of catalyst); while other additives (i.e., binders, diluents, and the like) are suitably employed at significantly higher levels (i.e., as a significant percentage of the total catalyst weight).

Supported catalysts can be prepared employing techniques well known to those of skill in the art, e.g. by precipitation of active materials on the support, by impregnation, by coprecipitation of support and active materials, or by grinding together the support and active material(s) in particulate form.

The process temperature, pressure and contact time are not critical. One uses a temperature at which isomerization to form the desired product takes place. The process can be conducted at any convenient pressure. The reaction (contact) time is not a truly independent variable, but is dependent at least to some extent on the other reaction variables employed, such as the process temperature, the inherent reactivity of the epoxide, the activity of the catalyst, etc. The process temperature, pressure, and time of reaction are discussed in more detail below.

Suitable reaction temperatures generally fall within the range of about 100° C. up to about 200° C. At lower temperatures, the reaction may proceed so slowly as to be impractical, while at higher temperatures undesirable levels of by-products, might be obtained. Preferred reaction temperatures fall within the range of about 110° C. up to about 175° C.

The reaction pressure can be within a wide range. Typically pressures of about 0.1 to about 100 atmospheres are selected, primarily as a function of safety, handling, equipment availability, and other practical considerations. Preferably, the reaction pressure is maintained in the range of about 1 up to 30 atmospheres.

Because the process of this invention is exothermic in most instances, it is preferred that the epoxide not be contacted neat with the catalyst. In other words, it is preferred that the epoxide be admixed with a diluent. Suitable diluents are inert under the reaction conditions employed. Examples of diluent gases useful in this invention include methane, ethane, nitrogen, helium, argon, neon, carbon dioxide, and the like. It is preferred that the partial pressure of the epoxide be in the range of from about 0.01 to about 0.5. When the process is conducted in the liquid phase, a saturated hydrocarbon can be used as the inert reaction medium. Any convenient concentration of epoxide in the inert liquid can be used, e.g. from about 0.1 to 50 weight percent.

A wide range of contact times can be used for the practice of the present invention within wide ranges. Generally, the epoxide and catalyst are maintained in contact for a time sufficient to obtain epoxide conversions in the range of about 0.5 up to 95 mole percent or higher. Epoxide conversions can be varied to give the most efficient utilization of reactor capacity.

Those of skill in the art recognize that the actual contact times required to accomplish the desired conversion levels can vary within wide ranges, depending on such factors as vessel size, epoxide to diluent ratios, the loading level on the catalyst, the presence or absence of any catalyst modifiers (and their loading levels), the reaction temperature and pressure, and the like.

The invention process can be carried out in either batch or continuous mode. Continuous reaction is presently preferred since high reactor throughput and higher purity product is obtained in this manner. The batch mode is satisfactorily employed when high volume of reactant throughput is not required, for example, for liquid phase reactions.

For a continuous mode of reaction carried out in the gas phase, typical gas hourly space velocities (GHSV) fall within the range of about 100 up to 30,000 hr$^{-1}$. GHSV in the range of about 200 up to 20,000 hr$^{-1}$ are preferred, with GHSV in the range of about 300 up to 10,000 hr$^{-1}$ being most preferred.

When a continuous mode of reaction is carried out in the liquid phase, typical liquid hourly space velocities (LHSV) employed will give contact times analogous to that obtained at the GHSV values given above. Most preferably, LHSV employed will fall in a range so as to produce a desirable combination of feed epoxide conversion levels and high product selectivity.

Recovery of product produced in the practice of the present invention can readily be carried out employing techniques well known by those of skill in the art. For example, where reaction is carried out in the continuous mode, unreacted starting material is initially separated from reaction products; and the desired product then isolated from the resulting product mixture by distillation, crystallization, extraction, or the like.

EXAMPLES

In all of the following runs, the processes were carried out under steady state conditions in a one atmosphere, single-pass, flow reactor system. The reactor tube was constructed of Pyrex, and the catalyst charge (between 0.1 and 20 grams) was held in place by means of a Pyrex frit. The reactor tube was housed inside a vertical, split tube furnace controlled by a temperature controller, which maintained the reaction temperature over the desired range. All feed inlet lines and reactor exit lines were maintained at 120° C. to prevent condensation of feed or product components. The geometric design of the reactor and of the catalyst particles, as well as the bed depth were chosen to maintain and measure the true kinetic and catalytic aspects of the reaction being investigated. Gas hourly space velocities for all experiments fell within the range of from 200 to 4000 hr$^{-1}$. A chromel/alumel thermocouple sheathed in stainless steel was embedded within the catalyst bed to measure the actual temperature of reaction.

The epoxide feed, butadiene monoxide, was added as a vapor by bubbling helium (an inert carrier gas) through a liquid/vapor saturator maintained at constant temperature to ensure constant and reproducible partial pressure of the epoxide in the helium stream. The temperature of the saturator was held constant at a pre selected temperature within the range of from $-10°$ C. to 20° C., to give a partial pressure of the epoxide vapor within the range of from 0.03 to 0.17 atmosphere, in the helium diluent. The helium flow rate was maintained by using a mass flow controller. The device permitted accurate and reproducible helium flow rates in the range of 0–200 ml (STP)/min.

Reaction product analysis, and analysis of the feed composition, were made using an in-line, gas sampling loop connected directly to the inlet of a Varian 3760 gas chromatograph. Unreacted feed and reaction products were separated using a packed glass column (eight feet long and 2 mm inside diameter) of Chromosorb 102 porous polymer packing. A flame ionization detector gave quantitative analysis of the various reaction products. In many instances, the feed epoxide and the crotonaldehyde were the only organics present in the product stream.

Results and reaction conditions are summarized in the following table. For the supported catalysts, the weight loading is specified as weight of metal or hydrogen halide per total weight of finished catalyst, the weight loading being expressed as percentage.

TABLE

| Example | Catalyst | Temp. °C. | Space Velocity (hr$^{-1}$) | Butadiene Monoxide Conversion % | Selectivity to Crotonaldehyde, %** |
|---|---|---|---|---|---|
| 1 | 7.5% LiI/MgO | 125 | 2300 | 17 | 60 |
| 2 | ''* | 155 | 2300 | 34 | 64 |
| 3 | 7.5% KI/MgO | 175 | 2500 | 15 | 71 |
| 4 | 7.5% HI/ZnO | 110 | 200 | 28 | 100 |
| 5 | '' | 120 | 400 | 22 | 100 |
| 6 | '' | 140 | 1000 | 100 | 100 |
| 7 | 36% HI/ZnO | 100 | 200 | 19 | 100 |
| 8 | '' | 120 | 1000 | 15 | 100 |
| 9 | '' | 150 | 1000 | 100 | 100 |
| 10 | '' | 163 | 4000 | 65 | 100 |
| 11 | 7.5% LiI/ZnO | 110 | 340 | 7 | 61 |
| 12 | '' | 120 | 400 | 22 | 60 |
| 13 | 7.5% KI/ZnO | 220 | 1600 | 5 | 95 |
| 14 | 20% ZnI$_2$/ZnO | 130 | 600 | 88 | 100 |
| 15 | 1.5% LiI/ZnO | 112 | 300 | 12 | 80 |
| 16 | '' | 125 | 300 | 33 | 79 |
| 17 | 9% FeCl$_3$/Al$_2$O$_3$ | 129 | 1870 | 19 | 74 |
| 18 | 12% FeCl$_3$/SiO$_2$ | 155 | 1500 | 6 | 100 |
| 19 | 20% FeCl$_3$/MgO | 162 | 2000 | 20 | 96 |
| 20 | Unsupported ZnCl$_2$ | 162 | 3000 | 57 | 65 |

*Where ditto marks are used in the second column of the Table, the catalyst is the same as the above. Thus in Example 2, the catalyst was 7.5% LiI supported on magnesium oxide.
**Selectivity expressed as molar selectivity, i.e., moles of crotonaldehyde formed based on moles of butadiene monoxide converted.

The processes employed in the above examples can be extended to the use of 4,4-dimethylbutadiene monoxide, and other alkyl butadiene monoxides where the alkyl groups are in the positions denoted as R and $R^1$ in the Formula (I). Examples include dimethylbutadiene monoxide up to and including di-n-butylbutadiene monoxide. Unsymmetrically substituted butadiene monoxides can also be employed.

The feed epoxides can be admixed with methane, ethane, nitrogen, carbon dioxide or helium as an inert gaseous diluent such that the partial pressure of the olefin epoxide is from 0.01 to 0.5. Thus for example using the above feed compositions, and a reaction pressure of 0.1 to 100 atmospheres, the corresponding aldehyde is produced using as a catalyst, LiI, KI, CsI, $BaCl_2$, $BaI_2$, $CuBr_2$, $CuCl_2$, $ZnI_2$, $ZnCl_2$, $AlCl_3$, $AlBr_3$, $ZrBr_4$, $ZrCl_4$, $TiCl_3$, $CrCl_3$, $MnCl_2$, $MnBr_2$, $FeCl_3$, $FeBr_3$, HCl, HBR, or HI, or mixtures of any of these. The catalyst is preferentially supported on a metal oxide so that the catalyst loading is 0.5–50 weight percent.

The invention has been fully described above with particular reference to preferred embodiments. It will be understood that modifications and substitutions thereof can be made without departing from the scope and spirit of the appended claims.

We claim:

1. Process for the preparation of an unsaturated aldehyde, said process comprising isomerizing a terminal epoxide having an olefinic double bond on a carbon atom adjacent to a carbon atom in the epoxide ring, said epoxide having the formula:

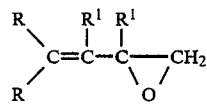

wherein each substituent indicated by R is selected from the class consisting of hydrogen and alkyl radicals having up to about 4 carbon atoms, and each substituent indicated by $R^1$ is selected from hydrogen and alkyl groups of up to about 2 carbon atoms, said process comprising contacting said epoxide at a temperature within the range of from about 100° C. to about 200° C., with a catalytic quantity of a catalyst selected from the class consisting of the chlorides, bromides and iodides of hydrogen, the iodides of alkali metals, and alkaline earth metals, and the chlorides and bromides of zinc, copper, aluminum, zirconium, titanium, vanadium, chromium, manganese and iron;

said unsaturated aldehyde product having the formula:

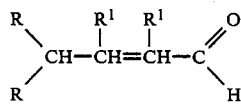

wherein R and $R^1$ each have the same significance as above.

2. An isomerization process of claim 1 wherein said catalyst is an alkali metal iodide.

3. An isomerization process of claim 1 wherein said catalyst is an iodide of a Group IIB metal.

4. An isomerization process of claim 1 wherein said catalyst is hydrogen iodide.

5. Process for the preparation of an unsaturated aldehyde from an unsaturated terminal epoxide having the formula:

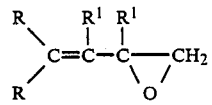

wherein each radical indicated by R is selected from hydrogen and alkyl radicals having up to about 4 carbon atoms, and each radical indicated by $R^1$ is selected from hydrogen and alkyl radicals having up to about 2 carbon atoms; said process comprising contacting said epoxide with a catalytic quantity of a catalyst selected from the class consisting of LiI, KI, CsI, $BaCl_2$, $BaI_2$, $CuBr_2$, $CuCl_2$, $ZnI_2$, $ZnCl_2$, $AlCl_3$, $AlBr_3$, $ZrBr_4$, $ZrCl_4$, $TiCl_3$, $CrCl_3$, $MnCl_2$, $MnBr_2$, $FeCl_3$, $FeBr_3$, HCl, HBR, and HI, at a temperature within the range of from about 100° to about 200° C.

said process being conducted in the vapor phase, in the presence of an inert diluent gas, and at a pressure within the range of from about one to about 100 atmospheres;

said unsaturated aldehyde product having the formula:

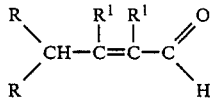

wherein R and $R^1$ have the same significance as above.

6. The process of claim 5 wherein said catalyst is on a metal oxide support such that the catalyst loading is from about 0.5 to about 50 weight percent.

7. The process of claim 6 wherein said catalyst is selected from the iodides of metals in Groups IA, IIA, and IIB of the Periodic Table.

8. The process of claim 6 wherein said catalyst is hydrogen iodide.

9. The process of claim 6 wherein said catalyst is selected from the chlorides and bromides of aluminum, titanium, vanadium, chromium, manganese, iron, copper and zinc.

10. The process of claim 6 wherein the epoxide is butadiene monoxide.

11. Process of claim 5 wherein the reaction pressure is from about 0.1 to about 30 atmospheres.

12. Process of claim 5 wherein said terminal epoxide is contacted with said catalyst in the vapor phase in the presence of a diluent, such that the partial pressure of the epoxide is from about 0.01 to about 0.5.

13. Process of claim 12 wherein the gas hourly space velocity is within the range of from about 100 to about 30,000 $Hr^{-1}$.

* * * * *